United States Patent
Forni et al.

(10) Patent No.: US 11,236,123 B2
(45) Date of Patent: Feb. 1, 2022

(54) METHOD FOR PREPARATION OF PEPTIDES WITH PSWANG LINKER

(71) Applicant: Polypeptide Laboratories Holding (PPL) AB, Limhamn (SE)

(72) Inventors: Luciano Forni, La Louvière (BE); Daniel Carbajo Lopez, Barcelona (ES); Fernando Albericio Palomera, Barcelona (ES)

(73) Assignee: Polypeptide Laboratories Holding (PPL) AB, Limhamn (SE)

( * ) Notice: Subject to any disclaimer, the term of this patent is extended or adjusted under 35 U.S.C. 154(b) by 0 days.

(21) Appl. No.: 16/071,344

(22) PCT Filed: Jan. 20, 2017

(86) PCT No.: PCT/SE2017/000006
§ 371 (c)(1),
(2) Date: Jul. 19, 2018

(87) PCT Pub. No.: WO2017/127007
PCT Pub. Date: Jul. 27, 2017

(65) Prior Publication Data
US 2020/0024306 A1    Jan. 23, 2020

Related U.S. Application Data

(60) Provisional application No. 62/280,871, filed on Jan. 20, 2016.

(30) Foreign Application Priority Data

| Jan. 20, 2016 | (EP) | 16152145 |
| Feb. 2, 2016 | (EP) | 16153974 |
| Feb. 2, 2016 | (EP) | 16154977 |
| Nov. 4, 2016 | (EP) | 16197210 |
| Nov. 4, 2016 | (EP) | 16197345 |

(51) Int. Cl.
| *C40B 50/08* | (2006.01) |
| *C07K 1/10* | (2006.01) |
| *C07K 1/02* | (2006.01) |
| *C07K 14/605* | (2006.01) |

(52) U.S. Cl.
CPC ........... *C07K 1/10* (2013.01); *C07K 1/026* (2013.01); *C07K 14/605* (2013.01)

(58) Field of Classification Search
None
See application file for complete search history.

(56) References Cited

U.S. PATENT DOCUMENTS

| 1,945,145 A | 1/1934 | Gordon |
| 3,214,393 A | 10/1965 | Sefton |
| 3,296,154 A | 1/1967 | Ferrigno |
| 3,566,758 A | 3/1971 | Perkins |
| 3,639,551 A | 2/1972 | Leach |
| 3,661,810 A | 5/1972 | Gahmig |
| 3,723,362 A | 3/1973 | Battigelli |
| 3,811,822 A | 5/1974 | Cherenson |
| 3,876,741 A | 4/1975 | Klein |
| 3,973,884 A | 8/1976 | Terminiello |
| 4,110,312 A | 8/1978 | Banucci et al. |
| 4,243,717 A | 1/1981 | Gahmig |
| 4,272,469 A | 6/1981 | Smith |
| 4,302,549 A | 11/1981 | Crowley |
| 4,398,958 A | 8/1983 | Hodson et al. |
| 4,450,022 A | 5/1984 | Galer |
| 4,617,219 A | 10/1986 | Schupack |
| 4,771,081 A | 9/1988 | Cox |
| 4,778,718 A | 10/1988 | Nicholls |
| 4,793,892 A | 12/1988 | Miller et al. |
| 4,816,091 A | 3/1989 | Miller |
| 4,841,702 A | 6/1989 | Huettemann |
| 4,916,004 A | 4/1990 | Esminger et al. |
| 5,132,060 A | 7/1992 | Stevens |
| 5,322,738 A | 6/1994 | Breidenbach |
| 5,350,554 A | 9/1994 | Miller |
| 5,385,698 A | 1/1995 | Bishop et al. |
| 5,555,698 A | 9/1996 | Mandish |
| 5,943,775 A | 8/1999 | Lanahan et al. |
| 5,977,195 A | 11/1999 | Craig et al. |
| 5,985,943 A | 11/1999 | Hahn et al. |
| 6,187,409 B1 | 2/2001 | Mathieu |
| 6,218,002 B1 | 4/2001 | Wehtje |

(Continued)

FOREIGN PATENT DOCUMENTS

| CN | 103087181 | 5/2013 |
| CN | 104045706 | 9/2014 |

(Continued)

OTHER PUBLICATIONS

Tam Int. J. Pepride Protein Res. 16. 1980, 412-425 (Year: 1980).*
Carbajo et al. "Pseudo-Wang Handle for the Preparation of Fully Protected Peptides. Synthesis of Liraglutide by Fragment Condensation", Organic Letters, vol. 21, No. 7, Apr. 5, 2019 pp. 2459-2463.
Fayna et al. "The synergy of ChemMatrix resin and pseudoproline building blocks renders RANTES, a complex aggregated chemokine", Biopolymers, John Wiley & Sons, Inc., vol. 84, No. 5 Jan. 1, 2006 pp. 566-575.
Guillier et al. "Linkers and cleavage strategies in solid-phase organic synthesis and combinatorial chemistry", Chemical Reviews, American Chemical Society, vol. 100, Jan. 1, 2000, pp. 2091-2157.
Supplementary European Search Report for EP17741733 dated Jun. 25, 2019, 3 pages.

(Continued)

*Primary Examiner* — Satyanarayana R Gudibande
(74) *Attorney, Agent, or Firm* — Dority & Manning, P.A.

(57) ABSTRACT

The invention discloses a method for the preparation of a peptide by liquid phase coupling of two fragments, an N-terminal fragment and a C-terminal fragment of the desired peptide, wherein the C-terminal fragment is protected on its C-terminal COOH by a psWang linker; the method is demonstrated with liraglutide wherein the C-terminal fragment carries the Palmitoyl-Glu-OtBu residue on the Lys.

21 Claims, No Drawings

Specification includes a Sequence Listing.

(56) References Cited

U.S. PATENT DOCUMENTS

| | | |
|---|---|---|
| 6,297,292 B1 | 10/2001 | Glueck et al. |
| 7,445,738 B2 | 11/2008 | Dubey et al. |
| 7,670,520 B2 | 3/2010 | Dubey |
| 7,794,221 B2 | 9/2010 | Dubey |
| 8,038,915 B2 | 10/2011 | Stivender |
| 9,005,506 B2 | 4/2015 | Horizono et al. |
| 9,410,321 B2 | 8/2016 | Ciuperca |
| 9,499,980 B2 | 11/2016 | Mathieu |
| 9,914,245 B2 | 3/2018 | Mathieu |
| 2002/0090871 A1 | 7/2002 | Ritchie et al. |
| 2004/0209060 A1 | 10/2004 | McGrady et al. |
| 2004/0220303 A1 | 11/2004 | Tang et al. |
| 2005/0059747 A1 | 3/2005 | Berghmans et al. |
| 2006/0201090 A1 | 9/2006 | Guevara et al. |
| 2006/0292358 A1 | 12/2006 | Robertson et al. |
| 2007/0261336 A1 | 11/2007 | Chiou |
| 2009/0004378 A1 | 1/2009 | Jones |
| 2009/0280328 A1 | 11/2009 | Masuda et al. |
| 2010/0088984 A1 | 4/2010 | Guevara et al. |
| 2011/0046349 A1 | 2/2011 | Giraud et al. |
| 2011/0065819 A1 | 3/2011 | Schips et al. |
| 2011/0251296 A1 | 10/2011 | Gondo et al. |
| 2012/0219815 A1 | 8/2012 | Schmidt et al. |
| 2012/0241073 A1 | 9/2012 | Wiest et al. |
| 2014/0350219 A1 | 11/2014 | Pan et al. |
| 2015/0076726 A1 | 3/2015 | Mathieu |

FOREIGN PATENT DOCUMENTS

| | | |
|---|---|---|
| EP | 2757107 | 7/2014 |
| WO | WO8603245 | 6/1986 |
| WO | WO9808871 | 3/1998 |
| WO | WO0055119 | 9/2000 |
| WO | WO0166485 | 9/2001 |
| WO | WO2011006644 | 1/2011 |
| WO | WO2014199397 | 12/2014 |
| WO | WO-2014199397 A2 * | 12/2014 ........... C07K 14/605 |
| WO | WO2016005960 | 1/2016 |

OTHER PUBLICATIONS

Tam et al. "Photolabile Multi Detachable P Alkoxybenzyl Alcohol Resin Supports for Peptide Fragment or Semi Synthesis", International Journal of Peptide and Protein Research, vol. 16, No. 5, 1980, pp. 412-425.

Verdie et al. "Solid Phase Synthesis of Hydroxypyrrolidine Derivative and its Use in Solid Phase Peptide Synthesis as a Constrained Statine Mimic", International Journal of Peptide Research and Therapeutics: formerly known as Letters in Peptide Science, vol. 13, No. 1-2, Mar. 9, 2007, pp. 337-343.

Wang et al. "Polystyrene resins cross-linked with di- or tri(ethylene glycol) dimethacrylates as supports for solid-phase peptide synthesis", Tetrahedron, Elsevier Science Publishers, vol. 62, No. 20, May 15, 2006 pp. 4948-4953.

Zhu et al. "Convergent Synthesis of Peptide Conjugates Using Dehydroalanines for Chemoselective Ligations", Organic Letters, vol. 3, No. 8, Apr. 1, 2001, pp. 1189-1192.

Pacyniak, The lost foam method pre-expansion process, Feb. 2010, Archives of Foundry Engineering, vol. 2, pp. 89-94.

International Search Report and Written Opinion for PCT/US2014/055745 dated Jan. 13, 2015, 15 pages.

International Search Report for PCT/SE2017/000006, dated Apr. 13, 2017, 4 pages.

Written Opinion for PCT/SE2017/000006, dated Apr. 13, 2017, 4 pages.

* cited by examiner

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Ala Glu Gly Thr Phe Thr Ser Asp Val Ser Ser Tyr Leu Glu Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Gln Ala Ala Lys Glu Phe Ile Ala Trp Leu Val Arg Gly Arg Gly
1               5                   10                  15

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Glu Phe Ile Ala Trp Leu Val Arg Gly Arg Gly
1               5                   10
```

METHOD FOR PREPARATION OF PEPTIDES WITH PSWANG LINKER

CROSS REFERENCE TO RELATED APPLICATIONS

This application is the U.S. National Stage entry of International Application Number PCT/SE2017/000006 having a filing date of Jan. 20, 2017, which claims the filing benefit of U.S. Provisional Application Ser. No. 62/280,871 having a filing date of Jan. 20, 2016, European Patent Application No. 16152145.5 having a filing date of Jan. 20, 2016, European Patent Application No. 16153974.4 having a filing date of Feb. 2, 2016, European Patent Application No. 16154977.9 having a filing date of Feb. 10, 2016, European Patent Application No. 16197210.4 having a filing date of Nov. 4, 2016, European Patent Application No. 16197345.8 having a filing date of Nov. 4, 2016, all of which are incorporated herein by reference in their entirety.

SEQUENCE LISTING

The instant application contains a Sequence Listing which has been filed electronically in ASCII format and is hereby incorporated by reference in its entirety. Said ASCII copy, created on Aug. 19, 2019, is named CONI-91-PCT-US-_SL.txt and is 1,778 bytes in size.

FIELD OF THE INVENTION

The invention discloses a method for the preparation of a peptide by liquid phase coupling of two fragments, an N-terminal fragment and a C-terminal fragment of the desired peptide, wherein the C-terminal fragment is protected on its C-terminal COOH by a psWang linker; the method is demonstrated with liraglutide wherein the C-terminal fragment carries the Palmitoyl-Glu-OtBu residue on the Lys[(20)].

BACKGROUND OF THE INVENTION

In convergent peptide synthesis, two fragments, the N-terminal fragment and the C-terminal fragment, of a desired peptide are synthesized by SPPS (solid phase peptide synthesis), thereafter these two fragments are coupled in liquid phase, that is by LPPS (liquid phase peptide synthesis). The disadvantage of this method is that the C-terminal COOH of the C-terminal fragment is obtained after cleavage from the resin after SPPS in its unprotected form. Therefore it first must be protected again before this C-terminal fragment can be used in the liquid phase coupling with the N-terminal fragment.

This reprotection of the C-terminal COOH of the C-terminal fragment after SPPS is an additional step with additional isolation, purification etc.

There is a need for a method for preparation of peptides with convergent peptide synthesis that does not require this reprotection of the C-terminal COOH of the C-terminal fragment after SPPS.

By the use of a psWang handle during the preparation by SPPS of the C-terminal fragment it is possible to isolate the C-terminal fragment already with the C-terminal COOH in a protected form after cleavage from the resin, thereby the described reprotection is no longer necessary.

The method can be applied to any peptide, be it a final target peptide or a peptide fragment or a peptide intermediate, bearing a C-terminal COOH residue.

The application of this method is illustrated with liraglutide. Liraglutide has the CAS number 204656-20-2 and is compound of formula (3) (SEQ ID NO: 3),

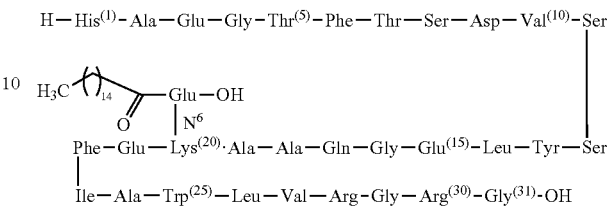

(3)

H—His[(1)]-Ala—Glu—Gly-Thr[(5)]-Phe—Thr—Ser—Asp—Val[(10)]-Ser

Phe—Glu—Lys[(20)]·Ala—Ala—Gln—Gly—Glu[(15)]-Leu—Tyr—Ser

Ile—Ala—Trp[(25)]—Leu—Val—Arg-Gly—Arg[(30)]-Gly[(31)]-OH the sequence can also be described as follows:
H-His[(1)]-Ala-Glu-Gly-Thr[(5)]-Phe-Thr-Ser-Asp-Val[(10)]-Ser-Ser-Tyr-Leu-Glu[(15)]-Gly-Gln-Ala-Ala-)) Lys[(20)] (Palmitoyl-Glu)-Glu-Phe-Ile-Ala-Trp[(25)]-Leu-Val-Arg-Gly-Arg[(30)]-Gly[(31)]-OH (SEQ ID NO: 3);
the numbers in parenthesis showing the numbering of the positions of the AA in the sequence as the numbering is used in instant invention.

WO 98/08871 A1 discloses a method for preparation of derivatives of GLP-1 and analogues thereof by culturing a host cell culture containing a DNA sequence encoding the polypeptide and capable of expressing the polypeptide in a suitable nutrient medium under conditions permitting the expression of the peptide, after which the resulting peptide is recovered from the culture.

WO 00/55119 A1 discloses the acylation of the epsilon-amino residue of Lys[(20)] of GLP-1 analogues with certain compounds useful as acylating agents. In this disclosure the N-terminal amino residue of GLP-1 analogues are not protected. The disadvantage is that diacylation occurs, both the N-terminal amino residue and the epsilon-amino residue of Lys[(20)] are acylated. The undesired by products need to be separated by purification.

WO 2011/006644 A2 discloses a convergent method for the preparation of exenatide, Exenatide is a peptide wherein the C-terminal is a carboxamide residue. In the method the peptide chain is split up into four sequential fragments P3-Frag1[1-10]-OH, P2-Frag2[11-21]-OH, P1-Frag3[22-29]-OH and H$_2$N-Frag4[30-39]-NH$_2$, and the peptide chain is build up by coupling of Frag3 with Frag4, then Frag 2 is coupled and then Frag 1 is coupled, these coupling are done in solution. The four fragments can be prepared by SPPS or by LPPS, preferably by SPPS. Especially Frag 4 with the C-terminal carboxamide residue, is prepared by SPPS either with a resin, which allows for the formation of the carboxamide directly after cleavage, such as a Sieber amide resin, or by using N-terminally protected serinamide, such as Fmoc-Ser-NH$_2$, and connecting its side chain to a resin, whereby again Frag1 after cleavage from the resin is directly formed with the C-terminal carboxamide residue. The other possibility is to couple N-terminally protected serinamide onto a fragment Frag5, Frag5 contains the amino acids 30 to 38. In any case this convergent synthesis strategy takes advantage of the fact that the target peptide has a C-terminal carboxamide residue, this acts in the LPPS fragment coupling a natural protecting group of the C-terminal COOH residue of the C-terminal fragment. Therefore this method is not generally applicable or transferable to any peptides, but only to peptides with a C-terminal carboxamide residue. Liraglutide for example does not have a C-terminal carboxamide residue, so applying the method of WO 2011/006644

A2 to Liraglutide would raise the problem of converting the C-terminal carboxamide residue back to a C-terminal COOH residue; the skilled person is aware that this is almost impossible without destruction of the peptide chain of Liraglutide.

WO 2016/005960 A1 discloses a process for the preparation of Liraglutide which includes:
a) introducing the spacer Palmitoyl-glutamyl-OtBu on side chain $NH_2$ of Lysine of fragment Fmoc-Lys(Alloc)-Glu(Otbu)-Phe-Ile-Ala-Trp(Boc)-Leu-Val-Arg(Pbf)-Gly-Arg(pbf)-Gly (SEQ ID NO: 4) attached to solid support;
b) coupling rest of the amino acid sequence from alpha amino group of Lysine of the fragment of Liraglutide obtained in step (a) to obtain Liraglutide attached to solid support;
c) cleavage of Liraglutide from the solid support.

As solid support are mentioned among others PS resin, or PS resin used by Wang with hydroxy-benzyl-p-benzyloxy moieties directly linked to the resin. The cleavage of the Liraglutide from the resin is done using strongly acidic conditions, mentioned are a cocktail mixture comprising TFA/Phenol/Thioanisole/Water/Triisopropyplsilane (TIS) in a ratio of about 82.5%, 5%, 5%, 2.5%, and 5% respectively, and also a cocktail mixture comprising TFA/Phenol/Water/TIS in a ratio of about 76.5%, 17.5%, 4.3%, and 1.7% respectively. These cocktails act simultaneously for peptide cleaving and for global deprotection. In Example 1 a Wang resin is used, the peptide is cleaved from the resin with a strongly acidic cocktail mixture of TFA (462.5 ml), TIPS (12.5 ml), Water (12.5 ml), and Phenol (12.5 ml) which provides simultaneously for global deprotection.

Wang, Y., et al, Tetrahedron 2006, 62, 4948-4953, discloses the Wang resin on page 4950 in Scheme 1 under Formula 2. The Wang resin is prepared by chloromethylation of a PS resin, followed by reaction with 4-hydroxybenzyl alcohol, providing a PS resin with hydroxy-benzyl-p-benzyloxy moieties directly linked to the resin. As already mentioned above, for cleavage of peptides from Wang resin strongly acidic conditions are required, Wang reports under 3.9 third paragraph for cleavage a treatment with TFA/thioanisole/water (95/2.5/2.5, v/v/v).

Garcia-Martin, F., et al., Biopolymers 2006, 84, 566-575, discloses the use of Wang resin for the preparation of the peptide RANTES. Again the cleavage of the peptide from the Wang resin and simultaneous global deprotection was done using strongly acidic conditions by treatment with a cocktail of TFA-phenol-$H_2O$-thioanisole-1,2-ethanedithiol, 82.5:5:5:5:2.5.

Verdie, P., et al., International Journal of Peptide Research and Therapeutics, 2007, 13, 337-343, discloses the use of Wang resin in SPPS. As required by the Wang resin, the resin-bound compound was treated for cleavage with a cleavage cocktail of TFA/TIS/$H_2O$ 95/2.5/2.5 v/v/v, representing the usual strongly acidic conditions required by Wang resin.

SPPS in general shows low yields compared to LPPS and therefore has the disadvantage that higher volumes of product are cost intensive, and the longer the chain is that needs to be prepared be SPPS, the lower is the yield. WO 2016/005960 A1 reports in example 1 a yield of 18 g of crude Liraglutide with a purity of 27.5% in its SPPS method which means 4.95 g of Liraglutide, which means 1.3 mmol based on a MW of 3751.2 g/mol. The first amino acid Fmoc Gly was used in the SPPS in a quantity of 240 mmol, indicating a yield of 0.5% based on the first amino acid, the next amino acids were in a quantity of 80 mmol, indicating a yield of 1.6% based on these next amino acids.

In the method of instant invention the yield for the exemplified Liraglutide was 50% based on the loading capacity of the resin with 85% purity in case of the protected fragment 2 comprising the palmitoyl chain. The amino acids were used in an amount of 3 eq based on the loading capacity of the resin, which means in an excess of 7.1 of the amino acids used with regard to the yield of fragment 2, so the yield of fragment 2 based on the amino acids used was 14.1% and thereby significantly higher than in WO 2016/005960 A1. The yield of the fragment coupling of fragments 1 and 2 in solution and of the subsequent global deprotection was 100% each.

The use of Wang resin does not allow for a convergent strategy in such an efficient way as disclosed in instant invention: If two fragment were prepared on a Wang resin for later use in a liquid phase coupling of these two fragments, the cleavage from the Wang resin of the fragments results in fragments that have an unprotected C-terminal COOH residue; the peptide is cleaved from the hydroxy-benzyl-p-benzyloxy moieties which are directly linked to the resin. The C-terminal fragment of the desired peptide would need to be protected first on its C-terminal COOH residue before a fragment coupling reaction could be done. This means additional steps in the procedure.

Furthermore, especially in case of SPPS using the Fmoc/tBu protocol, cleavage from the Wang resin results in globally deprotected fragments, so a reprotection of the side chains of the amino acids would be necessary, if the fragments were to be used in a fragment coupling reaction in order to avoid interference of the side chains in the coupling reaction. Such a reprotection of side chain residues of a peptide is a highly challenging task, if possible at all. In any case it means additional steps in the procedure.

By the use of the psWang handle the target peptide can be split up into two or even more fragments, the individual fragments can be synthesized by SPPS, leading to higher yields since the chain length, that has to be synthesized by SPPS, is shorted compared to a full SPPS synthesis of the target peptide, cleavage from the resin is done under weakly acidic conditions, thereby avoiding the cleavage of any side chain protecting groups, and the respective C-terminal fragment can be cleaved from the resin in form of a C-terminal protected fragment with the psWang handle as protecting group, which avoids the additional steps of reprotecting its C-terminal COOH residue that comes off unprotected in case of respective conventional cleavage of peptides from resin, such as is the case when Wang resin is used.

So the method of instant invention avoids the step of reprotecting the C-terminal COOH residue of a peptide fragment after cleavage from a resin, when this fragment, subsequent to its synthesis by SPPS, is to be used as a C-terminal fragment in a LPPS coupling with another fragment.

In addition the use of Wang resin, due do the inherent global deprotection of the side chains which takes places simultaneously during cleavage of the fragment from the resin under the required strongly acidic conditions, does not at all allow the use of the thus formed fragments, since these fragments have unprotected side chains which render them incompatible for any subsequent fragment coupling reaction, be it by LPPS or by SPPS.

In case of liraglutide, another advantage of the method is that the Palmitoyl-Glu-OtBu residue on the Lys[(20)] of N-terminal fragment can be introduced onto the N-terminal fragment during SPPS and on-resin, while the N-terminal $NH_2$ is still protected. If it was introduced onto a fully deprotected liraglutide precursor that has not yet the Palmitoyl-Glu-OtBu residue, a method that could be derived from the disclosure of WO 00/55119 A1, then the N-terminal NH$_2$ first needs to be selectively protected before the Palmitoyl-Glu-OtBu residue can be introduced onto the Lys$^{(20)}$ in order to avoid diacylation. This required selective protection is additional difficulty, an additional source of impurities and introduces further steps in the synthesis of liraglutide.

In case of liraglutide, another advantage of the method is that the Palmitoyl-Glu-OtBu residue can be introduced with a good yield and with low side reactions by introducing it after the coupling of Ala$^{(18)}$ or after the coupling of Ala$^{(19)}$, thereby no or only low amounts of by products are formed, which would need to be separated.

In the text, the following meanings are used:
AA amino acid or amino acid residue, depending on context;
Acm acetamidomethyl;
Alloc allyloxycarbonyl protecting group;
Boc tert-butoxycarbonyl protecting group;
coupling also called coupling reaction;
CTC chlorotritylchloride;
DCM dichloromethane;
DIC Diisopropylcarbodiimide;
DIPEA N,N-diisopropylethylamine;
DMAP N,N-4-Dimethylaminopyridine;
DMF Dimethylformamide;
DMSO Dimethylsulfoxide;
Dnp dinitrophenyl;
eq equivalents;
Fmoc 9-fluorenylmethoxycarbonyl protecting group;
HAL 5-(4-hydroxymethyl-3,5-dimethoxyphenoxy)valeric acid;
HFIP hexafluoroisopropanol;
HMPB 4-(4-hydroxymethyl-3-methoxyphenoxy)butyric acid;
MIS 1,2-dimethylindole-3-sulfonyl;
N$^6$ N$^6$ denotes the NH$_2$ of the side chain of Lys;
LPPS Liquid Phase Peptide Synthesis;
Mtr 4-methoxy-2,3,6-trimethylphenylsulfonyl;
N-terminal NH$_2$ N-terminal amino function;
OxymaPure® Ethyl (hydroxyimino)cyanoacetate, CAS 3849-21-6, purchased from Luxembourg Bio Technologies;
Pal, Palm abbreviations for Palmitoyl;
Pbf 2,2,4,6,7-pentamethyldihydrobenzofuran-5-sulfonyl protecting group;
Pmc 2,5,7,8-pentamethylchroman-6-sufonyl;
psWang pseudo Wang linker, also called pseudo Wang handle, in case of covalent connection to a resin or to a peptide it is also called a psWang residue;
PyBOP benzotriazol-1-yl-oxytripyrrolidinophosphonium hexafluorophosphate;

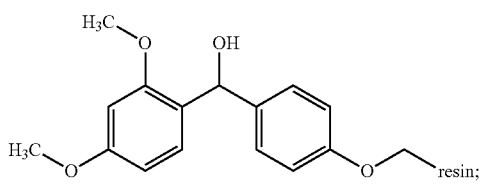

Rink acid resin Rink acid resin
RT room or ambient temperature;

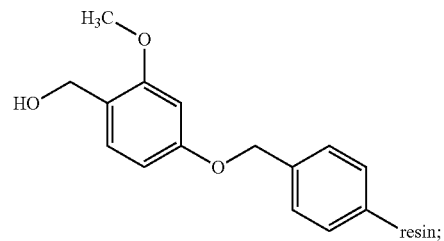

SASRIN resin SASRIN resin
SPPS Solid Phase Peptide Synthesis;
tBu tert butyl or tBu protecting group;
OtBu tert butyl ester;
TFA trifluoroacetic acid;
TFE trifluoroethanol;
TIS triisopropylsilane;
Trt trityl protecting group;
Z benzyloxycarbonyl;
if not otherwise stated.

SUMMARY OF THE INVENTION

Subject of the invention is a method for the preparation of a peptide PEP which comprises a coupling in liquid phase of two peptide fragments, an N-terminal fragment FRAG1 of PEP and a C-terminal fragment FRAG2 of PEP, that is by liquid phase peptide synthesis;
wherein the C-terminal COOH of FRAG2 is protected by a psWang residue;
the psWang residue is residue of formula (psWang);

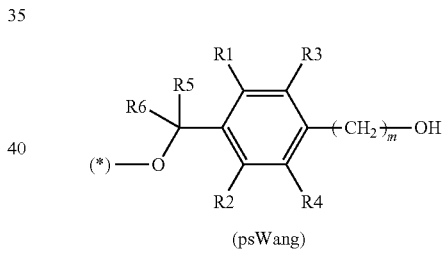

(psWang)

wherein the (*) denotes the covalent bond to the C atom of the CO residue of the C-terminal COOH of FRAG2;
R1, R2, R3 and R4 are identical or different and independently from each other selected from the group consisting of H, $C_{1-4}$ alkyl, $C_{1-4}$ alkoxy, CN, F, Cl and Br;
R5 and R6 are identical or different and are independently from each other H or $C_{1-4}$ alkyl;
m is 0, 1, 2, 3, 4, 5, 6, 7, 8, 9 or 10.

DETAILED DESCRIPTION OF THE INVENTION

Preferably, R1, R2, R3 and R4 are identical or different and independently from each other selected from the group consisting of H, $C_{1-2}$ alkyl, $C_{1-2}$ alkoxy and Cl; and
R5 and R6 are identical or different and are independently from each other H or $C_{1-2}$ alkyl. More preferably, R1, R2, R3 and R4 are identical or different and independently from each other selected from the group consisting of H, methyl, methoxy and Cl; and
R5 and R6 are identical or different and are independently from each other H or methyl. Even more preferably at least two of the substituents R1, R2, R3 and R4 are H.

In particular, at least three of the substituents R1, R2, R3 and R4 are H. More particularly, R5 and R6 are H. Even more particularly, R1, R2, R3, R4, R5 and R6 are H.

Preferably, in case that m is not 0 then at least one of the substituents R1, R2, R3 and R4 is $C_{1-4}$ alkoxy, more preferably $C_{1-2}$ alkoxy, even more preferably methoxy.

In another preferred embodiment, in case that m is not 0 then R5 and R6 are not H.

Preferably, m is 0, 1, 2, 3 or 4; more preferably, m is 0, 1 or 2; most preferably, m is 0.

In particular, m is 0 and R1, R2, R3, R4, R5 and R6 are H, thereby the psWang residue is the p-hydroxymethylphenol residue, the residue of formula (psWang-1);

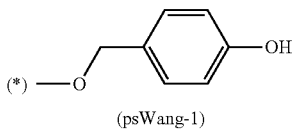

(psWang-1)

wherein the (*) denotes the covalent bond to the C atom of the CO residue of C-terminal COOH of FRAG 2.

The psWang residue is derived from the unconnected psWang linker, which is compound of formula (psWang-LINK);

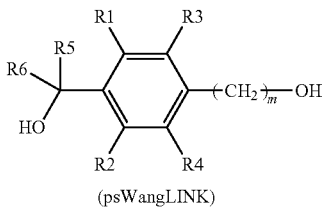

(psWangLINK)

with m, R1, R2, R3, R4, R5 and R6 as defined herein, also with all their embodiments.

Preferably, FRAG2 is prepared by SPPS. Preferably, FRAG2 is prepared by SPPS using Fmoc protocol, that is Fmoc protection of the alpha amino residues of the amino acid building blocks. More preferably, FRAG2 is prepared by SPPS wherein the C-terminal amino acid residue is covalently connected to the psWang residue, and the psWang residue is covalently connected to the resin used for the SPPS. Even more preferably, FRAG2 is prepared by SPPS wherein the alpha COOH of the C-terminal amino acid residue is covalently connected to the psWang residue, and the psWang residue is covalently connected to the resin used for the SPPS. Preferably, FRAG2 is prepared by SPPS on a resin used for the SPPS loaded with the psWang linker. Preferably, the psWang linker or the psWang residue respectively is connected to the resin used for the SPPS by an ether bond ETHBOND2; so the resin used for the SPPS of FRAG2 is a resin that allows to connect the psWang linker or the psWang residue respectively to the resin by ETHBOND2.

Especially, FRAG2 is prepared by SPPS on a resin loaded with the psWang linker by firstly covalently bonding the psWang linker onto the resin by ETHBOND2, this is done by an etherification reaction ETHERREAC forming ETHBOND2. Thereafter preferably the C-terminal AA of FRAG2 is covalently bonded to the psWang linker that is on the resin, this is done by an esterification reaction, thereafter the other AA are coupled by SPPS onto the C-terminal AA and then onto the growing peptide chain respectively.

Preferably, ETHBOND2 is cleavable under weakly acidic conditions, with the weakly acidic conditions as described herein; so the resin used for the SPPS of FRAG2 is a resin, that allows ETHBOND2 to be cleaved under weakly acidic conditions.

Preferably, ETHERREAC is done in the presence of a base. Suitable bases are for example trialkylamines, like N,N-diisopropylethylamine (DIPEA) or triethylamine (TEA); N,N-dialkylanilines, like N,N-diethylaniline; 2,4,6-trialkylpyridines, like 2,4,6-trimethylpyridine; and N-alkylmorpholines, like N-methylmorpholine.

Preferably, ETHERREAC is done in the presence of DIPEA as a base.

Preferably, the molar amount of base is from 1 to 10 times of the molar loading capacity of the resin.

Preferably, ETHERREAC can be done in any inert solvent which can dissolve the reactants. Preferred solvents for the coupling are water-miscible solvents like dimethyl sulfoxide (DMSO), dioxane, tetrahydrofurans such as tetrahydrofurane (THF) or methyltetrahydrofurane (Methyl-THF), 1-methyl-2-pyrrolidone (NMP), N,N-dimethylformamide (DMF), N,N-dimethylacetamide (DMA), or any mixture thereof; and non water-miscible solvents like dichloromethane (DCM), ethyl acetate or any mixture thereof; and any suitable mixture between water-miscible and non water-miscible solvents, including mixtures with water.

More preferably, ETHERREAC is done in a solvent selected from the group consisting of DMSO, dichloromethane, Me-THF, DMF, NMP, and mixtures thereof.

Preferably, the ETHERREAC is done at atmospheric pressure. Preferably, the reaction temperature of the ETHERREAC is from −20 to 70° C.; more preferably from −5 and 40° C., even more preferably from 0 to 35° C.

Preferably, the reaction time of the ETHERREAC is from 30 min to 12 h, more preferably from 30 min to 6 h, even more preferably from 30 min to 4 h.

The covalent bonding during SPPS of the alpha COOH of the C-terminal AA of FRAG2 to the psWang, and the covalent bonding of the psWang residue to the resin, are shown in formula (FRAG2-psWang-RESIN).

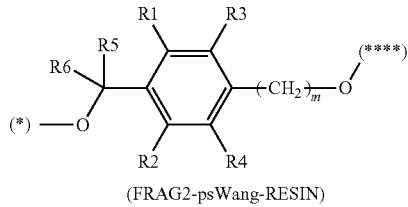

(FRAG2-psWang-RESIN)

wherein
the (*) denotes the covalent bond to the C atom of the CO residue of the alpha COOH of the C-terminal AA of FRAG2;
the (****) denotes the covalent bond to the resin, preferably ETHBOND2;
with m, R1, R2, R3, R4, R5 and R6 as defined herein, also with all their embodiments.

Preferably, the method comprises two steps, a step STEP1 and a step STEP2; STEP1 comprises the coupling of FRAG1 and FRAG2 by liquid phase peptide synthesis; STEP 1 provides a peptide PEP-psWang; STEP2 comprises cleavage of psWang from PEP-psWang obtained in STEP. Preferably, STEP2 provides PEP.

Preferably, FRAG1 and FRAG2 independently from each other have up to 250, more preferably up to 200, even more preferably up to 150, especially up to 100, more especially up to 75, even more especially up to 50, in particular up to 30, more in particular up to 20, amino acid residues. Preferably, FRAG1 and FRAG2 independently from each other have at least 2, 3, 4 or 5 amino acid residues. Any of the possible minimum number of amino acid residues can be combined with any of the possible maximum number of amino acid residues of FRAG1 and FRAG2.

Preferably, the N-terminal $NH_2$ of FRAG1 is protected by a protecting group PROTGN during the coupling of FRAG 1 and FRAG2. PROTGN can be any protecting group suitable for protecting the N-terminal $NH_2$ of FRAG 1. Commonly used PROTGN include protecting groups such as Boc, Fmoc, acetyl, Z or Trt. More preferably, PROTGN is Boc. Preferably, STEP 1 provides the peptide PROTGN-PEP-psWang.

Preferably,
FRAG1 is

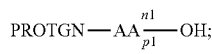

PROTGN—AA$_{p1}^{n1}$—OH;

and
FRAG2 is

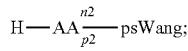

H—AA$_{p2}^{n2}$—psWang;

p1 is an integer from 2 to 50 and denotes the total number of amino acid residues of FRAG1;
p2 is an integer from 2 to 50 and denotes the total number of amino acid residues of FRAG2;
n1 is an integer from 1 to p1 and denotes the amino acid residue in position n1 of FRAG1;
n2 is an integer from 1 to p2 and denotes the amino acid residue in position n2 of FRAG2;
$AA^{(n1)}$ and $AA^{(n2)}$ are the amino acid residues of FRAG1 and of FRAG2 on position n1 and on position n2 respectively, and are identical or different and independently from each other alpha amino acid residues.
Preferably,
  p1 is an integer from 2 to 30;
  p2 is an integer from 2 to 30;
more preferably,
  p1 is an integer from 2 to 20;
  p2 is an integer from 2 to 20.
Preferably, the amino acid residue of FRAG1 and FRAG2 are alpha amino acids residues which occur in natural peptides or in natural proteins. More preferably, the amino acid residue of FRAG1 and FRAG2 are selected from the group consisting of Ala, Arg, Asn, Asp, Cys, Glu, Gln, Gly, His, Ile, Leu, Lys, Met, Phe, Pro, Ser, Thr, Trp, Tyr and Val. Preferably, any amino acid residue of FRAG1 and FRAG2, that can be used in a side chain protected form, is used in a side chain protected form.

In case of side chain protected amino acid residue of FRAG1 and FRAG2, STEP1 provides side chain protected PEP-psWang.

Preferably, amino acid residues of FRAG1 and FRAG2, that can be used in a side chain protected form and that are side chain protected in STEP 1, are selected from the group consisting of Arg, Asn, Asp, Cys, Glu, Gln, His, Lys, Ser, Thr, Trp and Tyr.

The side chain protection of the side chains of the amino acid residues of FRAG1 and FRAG2 is preferably realized in form of side chain protection groups which are not cleavable under weakly acidic conditions, with the weakly acidic conditions as described herein.

Preferably, side chain protection of Cys is Trt or Acm. Preferably, side chain protection of Asn and Gln is Trt. Preferably, side chain protection of His is Trt or Dnp. Preferably, side chain protection of Glu and Asp is OtBu. Preferably, side chain protection of Thr, Ser and Tyr is tBu. Preferably, side chain protection of Trp is Boc. Preferably, side chain protection of Arg is Pbf, Pmc, Mtr or MIS. Preferably, side chain protection of Lys is Alloc, Z or Boc.

More preferably, side chain protection of Cys, Asn, His and Gln is Trt; side chain protection of Glu and Asp is OtBu; side chain protection of Thr, Ser and Tyr is tBu; side chain protection of Trp is Boc; side chain protection of Arg is Pbf; side chain protection of Lys is Alloc.

Val and Ser, when they occur in the sequence of FRAG1 or of FRAG2 on adjacent positions as $Val^{(n1)}$ and $Ser^{(n1+1)}$ or as $Val^{(n2)}$ and $Ser^{(n2+1)}$ respectively, can also be used in the protected form of a pseudoproline Val-Ser[Psi$^{(Me,Me)}$Pro]-OH.

Also other possible pseudoprolines can be used, depending on the sequence of FRAG1 and FRAG2.

Cleavage of any PROTGN and of psWang, and the cleavage of any side chain protecting group, also the cleavage of the tBu protecting group on the alpha COOH of the Glu of the Palmitoyl-Glu-OtBu residue, can be done separately or simultaneously. The cleavage is preferably done in STEP2. When the cleavage is done simultaneously, then the cleavage is usually called global deprotection.

The conditions of such cleavage reactions are known to the skilled person and are dependent on the nature of protecting group. Many protecting groups require acidic conditions for cleavage, preferably strongly acidic conditions, with the strongly acidic conditions as defined herein, other protecting groups such as Z require cleavage by catalytic hydrogenation. Strongly acidic conditions means, in the context if this invention, using for cleavage a mixture of from 50 to 100%, preferably from 60 to 100%, more preferably from 70 to 100%, even more preferably from 80 to 100%, of TFA with a component COMPSTRONG, the % are vol-% and are being based on the total volume of the mixture of TFA and COMPSTRONG. Therefore, TFA can also be used neat. Preferably, COMPSTRONG is selected from the group consisting of SOLVSTRONG, phenol, water, TIS and a mixture thereof; SOLVSTRONG is solvent that is inert against TFA. Preferably, SOLVSTRONG is DCM. More preferably, COMPSTRONG is a mixture of phenol and TIS or a mixture of phenol, water and TIS.

Preferably, the volume ratios of a mixture TFA:water:TIS are
TFA: from 80 to 98;
water: from 1 to 10;
TIS: from 1 to 10;
the individual volume ratios of the three components adding up to 100.

Preferably, the volume ratios of a mixture TFA:phenol:water:TIS are
TFA: from 70 to 97;
phenol: from 1 to 10;

water: from 1 to 10;
TIS: from 1 to 10;
the individual volume ratios of the four components adding up to 100.

Preferably, the total amount of the mixture is from 5 to 20 ml per g of protected peptide.

Preferably, the cleavage is done at atmospheric pressure.

Preferably, the reaction temperature of the cleavage is from −20 to 70° C.; more preferably from −15 and 40° C., even more preferably from −15 to 35° C.

Preferably, the reaction time of the cleavage is from 30 min to 12 h, more preferably from 30 min to 6 h, even more preferably from 30 min to 4 h.

Any SPPS can be done on any conventional resin. Preferably, the resin for the SPPS of FRAG2 is a resin that allows to connect the psWang linker covalently to the resin with an ETHBOND2; more preferably, with an ETHBOND2 that is cleavable under weakly acidic conditions, with the weakly acidic conditions as defined herein.

Preferably, FRAG1 is prepared by SPPS.

Preferably, FRAG1 is prepared by SPPS using Fmoc protocol, that is, Fmoc protection of the alpha amino residues of the amino acid building blocks.

Preferably, the C-terminal amino acid of FRAG1 is connected to the resin used for the SPPS with an ester bond ESTBOND1; so the resin used for the SPPS of FRAG1 is a resin that allows to connect the C-terminal amino acid of FRAG1 to the resin with ESTBOND1.

Preferably, ESTBOND1 is cleavable under weakly acidic conditions, with the weakly acidic conditions as defined herein.

Preferably, the alpha COOH of the C-terminal AA of FRAG1 is covalently connected to the resin used for the SPPS.

Resins used for SPPS, that allow to connect covalently to the resin the psWang linker with an ETHBOND2 or the C-terminal amino acid of FRAG1 with an ESTBOND1 respectively, that are cleavable under weakly acidic conditions, with the weakly acidic conditions as defined herein, are for example CTC resin, Rink acid resin, SASRIN resin, resin modified with HAL and resin modified with HMPB.

Preferably, SPPS is done on a resin selected from the group consisting of CTC resin, Rink acid resin, SASRIN resin, resin modified with HAL and resin modified with HMPB; wherein the Rink acid resin, the SASRIN resin, the resin modified with HAL and the resin modified with HMPB are used in their chlorinated or brominated form. Chlorinated and brominated form means that the reactive OH of the resins or of the HAL or of the HMPB, respectively, onto which the psWang or the AA is coupled, is exchanged against a Cl or a Br. Preferably, SPPS is done on a CTC resin.

More preferably, FRAG1 and FRAG2 are prepared by SPPS on a CTC resin.

Even more preferably, FRAG2 is prepared by SPPS on a CTC resin that has been loaded with the psWang linker prior to the coupling of the C-terminal AA to the CTC resin.

Preferably, the resins used in the SPPS show a loading capacity of from 0.5 to 2 mmol of reactive sites per g resin.

Preferably, any SPPS is done by stepwise coupling of the individual amino acids.

Preferably, FRAG1 and FRAG2 are prepared by SPPS using Fmoc/tBu strategy; with Fmoc as protecting group for the alpha $NH_2$ of the amino acids used in the SPPS; more preferably except for the N-terminal amino acid of FRAG 1, where the alpha $NH_2$ is protected with PROTGN.

Weakly acidic conditions means, in the context if this invention, using for cleavage a mixture of from 0.01 to 25%, preferably from 0.01 to 15%, more preferably from 0.05 to 10%, even more preferably from 0.1 to 7.5%, TFA in a solvent SOLVWEAK, the % are vol-% and are being based on the total volume of the mixture of TFA and SOLVWEAK. SOLVWEAK is any solvent which is inert against TFA. Preferably SOLVWEAK is DCM, methyl THF or a mixture thereof. Preferably, the total amount of the mixture is from 5 to 20 ml per g of protected peptide. Preferably, the cleavage is done at atmospheric pressure.

Preferably, the reaction temperature of the cleavage is from −20 to 70° C.; more preferably from −15 and 40° C., even more preferably from −15 to 35° C.

Preferably, the reaction time of the cleavage is from 5 min to 12 h, more preferably from 5 min to 6 h, even more preferably from 10 min to 4 h.

Cleavage under weakly acidic conditions can also be done using TFE or HFIP instead of TFA. Preferably, ESTBOND1 and ETHBOND2 are cleaved under weakly acidic conditions.

In one embodiment, PEP is liraglutide, and the (*) in formula (psWang) denotes the covalent bond to the C atom of the CO residue of $Gly^{(31)}$ of liraglutide; also with all the embodiments described herein.

Preferably,
FRAG1 is Boc-$H^{(1)}$ $AEGT^{(5)}$ $FTSDV^{(10)}$ $SSYLE^{(15)}$ $G^{(16)}$-OH (SEQ ID NO: 1); and
FRAG2 is H-$Q^{(17)}$ $AAK^{(20)}$ (Palmitoyl-Glu-OtBu) $EFIAW^{(25)}$ $LVRGR^{(30)}$ $G^{(31)}$-psWang (SEQ ID NO: 2).

FRAG1 can also be depicted as Boc-[1-16]-OH or as compound of formula (I).

$$\text{Boc-H-[2-15]-G-OH} \tag{I}$$

FRAG2 can also be depicted as H-[17-31]-psWang or as compound of formula (II);

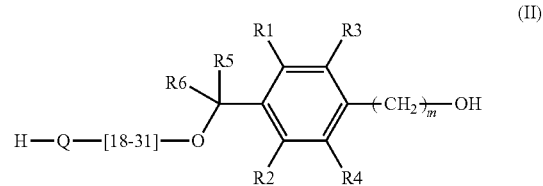

with m, R1, R2, R3, R4, R5 and R6 as defined herein, also with all their embodiments.

Liraglutide with psWang protection on the C-terminal COOH can also be depicted as compound of formula (III);

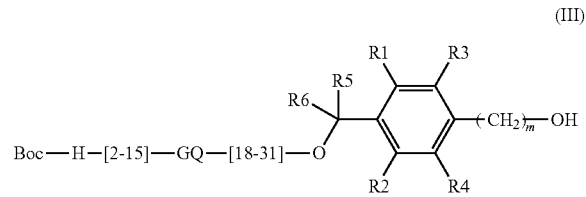

with m, R1, R2, R3, R4, R5 and R6 as defined herein, also with all their embodiments.

Preferably, $Val^{(10)}$ and $Ser^{(11)}$ are present in FRAG1 of liraglutide in form of a pseudoproline $Val^{(10)}$-$Ser^{(11)}$ ($psi^{Me,Me}Pro$).

More preferably, FRAG1 has the sequence Boc-His$^{(1)}$(Trt)-Ala-Glu(OtBu)-Gly-Thr$^{(5)}$ (tBu)-Phe-Thr(tBu)-Ser(tBu)-Asp(OtBu)-[Val$^{(10)}$-Ser(psi$^{Me,Me}$Pro)]-Ser(tBu)-Tyr(tBu)-Leu-Glu$^{(15)}$(OtBu)-Gly$^{(16)}$-OH(SEQ ID NO: 1), and is also called protected fragment 1.

More preferably, FRAG2 has the sequence H-Gln$^{(17)}$(Trt)-Ala-Ala-Lys$^{(20)}$ (Palmitoyl-Glu-OtBu)-Glu(OtBu)-Phe-Ile-Ala-Trp$^{(25)}$ (Boc)-Leu-Val-Arg(Pbf)-Gly-Arg$^{(30)}$(Pbf)-Gly-psWang (SEQ ID NO: 2), and is also called protected fragment 2.

In case of liraglutide, preferably, Val$^{(10)}$ and Ser$^{(11)}$ are used in the SPPS of FRAG1 in form of pseudoproline Fmoc-Val-Ser[Psi$^{(Me,Me)}$Pro]-OH.

Preferably, the Palmitoyl-Glu-OtBu residue on the N$^6$ of the Lys$^{(20)}$ of FRAG2 is the residue of formula (PALGLU),

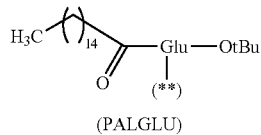

(PALGLU)

with the (**) in formula (PALGLU) denoting the covalent bond between the COOH of the side chain of the Glu and the N$^6$ of the Lys$^{(20)}$, and the Palmitoyl-Glu-OtBu residue is covalently bonded to the Lys$^{(20)}$ in a reaction REACPAL-GLU, wherein the NH$_2$ of the side chain of the Lys is reacted with a precursor of the residue of formula (PALGLU); preferably, REACPALGLU is done before FRAG2 is cleaved from the resin.

So REACPALGLU is done on-resin, that is REACPAL-GLU is done while FRAG2 or a precursor of FRAG2 is still covalently bonded to the resin. Preferably, the precursor of the residue of formula (PALGLU) is Pal-Glu(OSu)-OtBu, that is compound of formula (10);

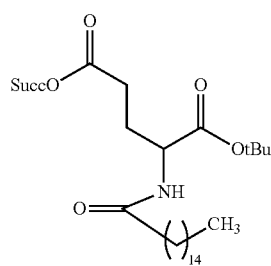

with SuccO being residue of formula (SuccO);

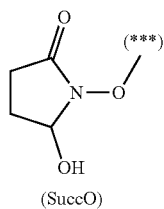

(SuccO)

wherein the (***) denotes the covalent bond to the CO residue in compound of formula (10).

Preferably, REACPALGLU is done after the coupling of Ala$^{(19)}$ or after the coupling of Ala$^{(18)}$, and before removal of the protecting group of the alpha NH$_2$ of Ala$^{(19)}$ or of Ala$^{(18)}$ respectively, preferably after the coupling of Ala$^{(18)}$.

Preferably, any protecting group of the side chain of Lys$^{(20)}$ is cleaved before REACPALGLU.

In case of liraglutide, preferably, Lys$^{(20)}$ is used in the SPPS of FRAG2 in form of Fmoc-Lys(Alloc)-OH; so the side chain protecting group of Lys$^{(20)}$, which is cleaved before REACPALGLU, is preferably Alloc. Preferably, cleavage of Alloc from the Lys$^{(20)}$ is done with a reaction CLEAVALLOC using Pd(PPh$_3$)$_4$ and PhSiH. CLEAVAL-LOC can be done in the presence of an additive ADDAL-LOC, ADDALLOC is selected from the group consisting of morpholine, 1,3-dimethylbarbituric acid, pyrrolidine, triphenylphosphine, dimedone, and mixtures thereof. Preferably, the molar amount of ADDALLOC is from 2 to 7 times of the molar amount of the Alloc residue. Preferably, the molar amount of Pd(PPh$_3$)$_4$ is from 0.01 to 10 times, more preferably from 0.02 to 5 times, even more preferably from 0.05 to 2 times, of the molar loading capacity of the resin.

Preferably, the molar amount of PhSiH is from 1 to 30 times, more preferably from 2 to 20 times, even more preferably from 5 to 15 times, of the molar loading capacity of the resin.

Preferably, CLEAVALLOC is done in a solvent selected from the group consisting of DMSO, dichloromethane, Me-THF, DMF, NMP, and mixtures thereof, more preferably the solvent is DCM. Preferably, CLEAVALLOC is done at atmospheric pressure. Preferably, the reaction temperature of CLEAVALLOC is from −20 to 70° C.; more preferably from −15 and 60° C., even more preferably from 5 to 35° C. Preferably, the reaction time of CLEAVALLOC is from 1 min to 2 h.

Preferably, any coupling is for the ease of reading also called COUPL, such as a SPPS coupling reaction or such as the LPPS coupling reaction of FRAG1 and FRAG2, and can be carried out using reaction conditions known in the art of peptide synthesis.

Preferably, coupling reagents, which can be used for COUPL and which are used in situ, are for example phosphonium or uronium coupling reagents, like benzotriazol-1-yloxy-tris(dimethylamino)phosphonium hexafluorophosphate (BOP), benzotriazol-1-yloxy-tris(pyrrolidino) phosphonium hexafluorophosphate (PyBOP), O-(benzotriazol-1-yl)-1,1,3,3-tetramethyluronium hexafluorophosphate (HBTU), O-(6-chlorobenzotriazol-1-yl)-1,1,3, 3-tetramethyluronium hexafluorophosphate (HCTU), O-(6-chlorobenzotriazol-1-yl)-1,1,3,3-tetramethyluronium tetrafluoroborate (TCTU), O-(7-azabenzotriazol-1-yl)-1,1,3, 3-tetramethyluronium hexafluorophosphate (HATU), O-(7-azabenzotriazol-1-yl)-1,1,3,3-tetramethyluronium tetrafluoroborate (TATU), O-(benzotriazol-1-yl)-1,1,3,3-tetramethyluronium tetrafluoroborate (TBTU), O-[cyano (ethoxycarbonyl)methylenamino]-1,1,3,3-tetramethyluronium tetrafluoroborate (TOTU) and (1-cyano-2-ethoxy-2-oxoethylidenaminooxy)dimethyl-amino-morpholino-carbenium hexafluorophosphate (COMU); or carbodiimide coupling reagents, like diisopropylcarbodiimide (DIC), dicyclohexylcarbodiimide (DCC) and water-soluble carbodiimides (WSCDI) like 1-ethyl-3-(3-dimethylaminopropyl)carbodiimide (EDC), optionally as salt like as hydrochloride salt.

Other coupling techniques use pre-formed active esters, such as N-hydroxysuccinimide (HOSu) and p-nitrophenol (HONp) esters, pre-formed symmetrical anhydrides, non-symmetrical anhydrides such as N-carboxyanhydrides (NCAs) and acid halides, such as acyl fluorides or acyl chlorides.

Preferred coupling reagents are carbodiimide coupling reagents and phoshonium coupling reagents, most preferred coupling reagents are selected from group consisting of PyBOP, DCC, DIC and EDC; more preferably, coupling reagent is PyBOP or DIC. EDC is preferably used as a salt, more preferably as EDC.HCl.

Preferably, the molar amount of coupling reagent is from 1 to 10 times, more preferably from 1 to 5 times, of the molar loading capacity of the resin, or of the molar amount of the fragment to be coupled in LPPS respectively. More preferably, the molar amount of coupling reagent is from 1 to 10 times, more preferably from 1 to 5 times, of the molar amount of the substrate, such as the AA, to be coupled, or of the molar amount of the fragment to be coupled in LPPS respectively.

COUPL can be done in the presence of a base, preferably a tertiary amine base, which both deprotonates the COOH residue of the carboxylic component and neutralizes any counterion of the $NH_2$ residue of the amino component in COUPL, and thus facilitates the coupling reaction.

Suitable bases are for example trialkylamines, like N,N-diisopropylethylamine (DIPEA) or triethylamine (TEA); N,N-dialkylanilines, like N,N-diethylaniline; 2,4,6-trialkylpyridines, like 2,4,6-trimethylpyridine; N,N-dialkylaminopyridines, like N,N-4-dimethylaminopyridine; and N-alkylmorpholines, like N-methylmorpholine. Preferably, COUPL is done in the presence of DIPEA as a base. Preferably, the molar amount of base is from 0.01 to 20 times, more preferably from 0.02 to 10 times, of the molar loading capacity of the resin, or of the molar amount of the fragment to be coupled in LPPS respectively. More preferably, the molar amount of base is from 0.01 to 20 times, more preferably from 0.02 to 10 times, of the molar amount of the substrate, such as the AA, to be coupled, or of the molar amount of the fragment to be coupled in LPPS respectively.

COUPL can be done in the presence of an auxiliary nucleophile as additive due to their positive effect in suppressing undesired side reactions. Any known auxiliary nucleophile may be used.

Examples of suitable auxiliary nucleophiles are ethyl (hydroxyimino)cyanoacetate, 1-hydroxybenzotriazole (HOBt), N-hydroxysuccinimide (HOSu), N-hydroxy-3,4-dihydro-4-oxo-1,2,3-benzotriazine (HOOBt) and 1-hydroxy-7-azabenzotriazole (HOAt). Preferably, HOBt or HOAt are used as auxiliary nucleophile. Preferably, the molar amount of auxiliary nucleophile is from 0.5 to 3 times of the molar amount of the amino residue that is to be coupled, or of the molar amount of the fragment to be coupled in LPPS respectively.

Especially, COUPL is done using DIC/OxymaPure, DCC/HOBt, EDC/HOBt, PyBOP/HOBt or EDC/HOAt. Preferably, COUPL can be done in any inert solvent which can dissolve the reactants. Preferred solvents for COUPL are water-miscible solvents like dimethyl sulfoxide (DMSO), dioxane, tetrahydrofurans such as tetrahydrofurane (THF) or methyltetrahydrofurane (Methyl-THF), 1-methyl-2-pyrrolidone (NMP), N,N-Dimethylformamide (DMF), N,N-Dimethylacetamide (DMA), or any mixture thereof; and non water-miscible solvents like dichloromethane (DCM), ethyl acetate or any mixture thereof; and any suitable mixture between water-miscible and non water-miscible solvents, including mixtures with water. More preferably, COUPL is done in a solvent selected from the group consisting of DMSO, dichloromethane, Me-THF, DMF, NMP, and mixtures thereof.

Preferably, the substrate in COUPL, for example any AA, that is reacted with the respective functional residue connected to the resin in SPPS, is preferably used in excess with regard to the molar loading capacity of the resin; more preferably, it is used in an molar amount of from 1 to 10 times, more preferably from 1 to 8 times, based on the molar loading capacity of the resin.

The two fragments, that are to be coupled in LPPS, are usually used in stoichiometric amounts with respect to each other, but of course one fragment can also be used in excess over the other one.

Preferably, COUPL is done at atmospheric pressure.

Preferably, the reaction temperature of COUPL is from −20 to 70° C.; more preferably from −15 and 40° C., even more preferably from −15 to 35° C.

Preferably, the reaction time of COUPL is from 30 min to 48 h, more preferably from 30 min to 24 h, even more preferably from 30 min to 12 h, especially from 30 min to 6 h.

Preferably, the progress of COUPL is monitored by HPLC and thereby the necessary reaction time is determined.

Preferably, the coupling of the first AA onto the resin in case of FRAG1 is an esterification reaction ESTERREACAA1. ESTERREACAA1 provides for ESTBOND1. The coupling of the first AA onto the psWang linker connected to a resin in case of FRAG2 is an esterification reaction ESTERREACAA2. Both ESTERREACAA1 and ESTERREACAA2 can be done with the reagents and the conditions as described for COUPL. ESTERREACAA1 can be done without using a coupling reagent.

Preferably, the molar amount of Pal-Glu(OSu)-OtBu in REACPALGLU is from 1 to 15 times, more preferably from 1 to 10 times, even more preferably from 1 to 5 times, of the molar loading capacity of the resin. REACPALGLU can be done in the presence of a base, preferably a tertiary amine base. Suitable bases are for example trialkylamines, like N,N-diisopropylethylamine (DIPEA) or triethylamine (TEA); N,N-dialkylanilines, like N,N-diethylaniline; 2,4,6-trialkylpyridines, like 2,4,6-trimethylpyridine; and N-alkylmorpholines, like N-methylmorpholine. Preferably, REACPALGLU is done in the presence of DIPEA as a base. Preferably, the molar amount of base is from 1 to 10 times, more preferably from 3 to 8 times, of the molar loading capacity of the resin. Preferably, REACPALGLU is done in a solvent selected from the group consisting of DMSO, dichloromethane, Me-THF, DMF, NMP, and mixtures thereof, more preferably the solvent is DCM. Preferably, REACPALGLU is done at atmospheric pressure. Preferably, the reaction temperature of REACPALGLU is from −20 to 70° C.; more preferably from −15 and 60° C., even more preferably from 5 to 35° C. Preferably, the reaction time of REACPALGLU is from 1 to 48 h, more preferably from 5 h to 24 h, even more preferably from 10 h to 24 h.

Fmoc cleavage is known to the skilled person, it is done with a base, preferably the base is a secondary amine, more preferably piperidine. The base is used in excess with regard to the molar loading capacity of the resin. Preferably, DMF is used as solvent in the Fmoc cleavage reaction. Preferably, the Fmoc cleavage is done at atmospheric pressure. Preferably, the reaction temperature of the Fmoc cleavage is from −20 to 70° C.; more preferably from −15 and 40° C., even more preferably from −15 to 35° C. Preferably, the reaction time of the Fmoc cleavage is from 1 min to 12 h, more preferably from 1 min to 6 h, even more preferably from 1 min to 1 h.

PEP can be isolated, preferably after a global deprotection, according to standard methods known to the skilled such as precipitation, preferably with ether, centrifugation, filtration etc. PEP can be purified according to standard methods known to the skilled person, such as HPLC.

A further subject of the invention is a peptide PEPTI, wherein the C-terminal COOH of PEPTI is protected by a psWang residue; with the psWang residue as defined herein, also with all its embodiments and definitions; wherein in the definition of the psWang residue the (*) denotes the covalent bond to the C atom of the CO residue of the C-terminal COOH of PEPTI.

Preferably, PEPTI has up to 500, more preferably up to 400, even more preferably up to 300, especially up to 200, more especially up to 150, even more especially up to 100, in particular up to 60, more in particular up to 40, amino acid residues. Preferably, PEPTI has at least 4, 5, 6, 7, 8, 9 or 10 amino acid residues.

Any of the possible minimum number of amino acid residues can be combined with any of the possible maximum number of amino acid residues of PEPTI.

PEPTI can be any peptide bearing said C-terminal psWang residue, such as a final target peptide or a peptide fragment or a peptide intermediate. Preferably, PEPTI is similar to or identical with FRAG2, also with all the definitions and embodiments of FRAG2 as defined herein. Preferably, PEPTI is prepared in the same way as described herein for FRAG2, also with all the embodiments as described herein for the preparation of FRAG2; so all the steps and details of the preparation of FRAG2 apply also for PEPTI.

PEPTI can be used for the preparation of peptides in the same way as described herein for the use of FRAG2 in the preparation of PEP, also with all the embodiments as described herein for the method for the preparation of PEP. Therefore further subject of the invention is the use of PEPTI for the preparation of peptides in LPPS.

EXAMPLES

AA

The SPPS was done with the following AA, if not stated otherwise:
Boc-His(Trt)-OH; Fmoc-Ala-OH; Fmoc-Glu(OtBu)-OH; Fmoc-Gly-OH; Fmoc-Thr(tBu)-OH; Fmoc-Phe-OH; Fmoc-Ser(tBu)-OH; Fmoc-Asp(OtBu)-OH; Fmoc-Tyr(tBu)-OH; Fmoc-Val-OH; Fmoc-Val-Ser[Psi$^{(Me,Me)}$Pro]-OH for position (10) and (11); Fmoc-Leu-OH; Fmoc-Gln(Trt)-OH; Fmoc-Lys(Alloc)-OH; Fmoc-Ile-OH; Fmoc-Trp(Boc)-OH; Fmoc-Arg(Pbf)-OH Pal-Glu(OSu)-OtBu, that is compound of formula (10), was purchased from IRIS Biotech.
Methods
Ninhydrin Test, Also Called Kaiser Test
The test is known to the skilled person, see Kaiser E. et al., Analytical Biochemistry 1970, 34, 595-598.
Solution 1: Dissolve 5 g ninhydrin in 100 mL ethanol.
Solution 2: Dissolve 40 g phenol in 10 mL ethanol.
Solution 3: Add 2 mL of a 0.001 M aq. KCN solution to 98 mL pyridine.
Procedure:
1. Wash resin with DCM (2 times).
2. Sample a few beads of resin in an Eppendorf tube.
3. Add one to two drops of each of the three solutions 1 to 3.
4. Mix well and heat to 120° C. for 3 to 5 min.
5. The presences of free resin-bound amines are indicated by blue resin beads.

Coupling
SPPS was done manually.
Washing
In the following examples washing with a solvent, such as DMF or DCM, was done by filtering the resin, suspending and stirring the resin in the solvent for a certain time and filtering again. For washes and Fmoc removal ca. 5 volumes of resin of the solvent was used; for couplings ca. 20 ml/g resin was used, if not stated otherwise. Stated in the examples are the number of repetitions of this washing cycle together with the time for stirring. Also in case of treating the resin with a reagent that is dissolved in a solvent this description of the number of repetitions of this treatment together with the time for stirring is used in the example, if not otherwise stated.
Yield
The yield was calculated on the basis of the synthesis scale with respect to resin loading capacity f and resin weight, if not otherwise stated.
Method for Determination of Purity
Peptide-resin (100 mg) is treated with ca. 2 ml of TFA:H$_2$O:TIS in the volume ratio 94:3:3 and stirring for 1 h at RT. The suspension is filtered. The deprotected peptide is precipitated by addition of diisopropyl ether (20 ml) to the filtrate. The purity of crude deprotected fragment is checked by HPLC:
(A) Determination of Purity of Fragment 1:
  Column with C18 stationary phase
  Mobile phase A: 0.1% (v/v) TFA in water
  Mobile phase B: 0.1% (v/v) TFA in acetonitrile
  Gradient: 5% (v/v) B to 100% (v/v) B in 11 min
  Temperature: RT
  Flow rate: 1 ml/min
  Detection: 254 nm
(B) Determination of Purity of Fragment 2:
  Column with C18 stationary phase
  Mobile phase A: 0.1% (v/v) TFA in water
  Mobile phase B: 0.1% (v/v) TFA in acetonitrile
  Gradient: 5% (v/v) B to 100% (v/v) B in 13 min
  Temperature: 40° C.
  Flow rate: 1 ml/min
  Detection: 254 nm
(C) Determination of Purity of Crude Liraglutide:
  Column with C18 stationary phase
  Mobile phase A: 0.1% (v/v) TFA in water
  Mobile phase B: 0.1% (v/v) TFA in acetonitrile
  Gradient: 5% (v/v) B to 100% (v/v) B in 11 min
  Temperature: RT
  Flow rate: 1 ml/min
  Detection: 254 nm
Fmoc Determination, Also Used for Determination of Resin Loading:
An analytical method based on the UV absorption of dibenzofulvene after cleavage of Fmoc on an aliquot of peptide-resin, the method is known to the skilled person. It can be done as follows:
An aliquot of loaded resin (ca. 100 mg) is washed with DMF (3 times with 5 ml) and DCM (3 times with 5 ml). It is then dried under vacuum.
10 mg of dried resin is added to a 2 mL polypropylene tube, 0.8 mL of DMF is added and the resin is allowed to swell for 10 minutes. Then 0.2 mL of piperidine is added, then the mixture is shaken for 20 min. Then 10 microL of the supernatant is pipetted into a quartz cuvette and is diluted with 0.990 mL of DMF. The absorbance at lamda=301 nm is determined. The piperidine-dibenzofulvene adduct that is formed upon Fmoc deprotection has a molar extinction coefficient of epsilon=7800 L×mol$^{-1}$×cm$^{-1}$; thus, the loading value is determined using Beer-Lambert law.

Apparent pH

The determination of the apparent pH is a way to measure the pH in an organic solvent (that is in a non aqueous solvent). The procedure is well known to the skilled person: One drop of the organic solvent or of the organic solvent solution is put on a wet pH paper stick, the resulting coloration gives the apparent pH.

Example 1: Synthesis of Liraglutide Using a Pseudo Wang Linker

Synthesis of Liraglutide using a pseudo Wang linker was done according to Scheme 1:

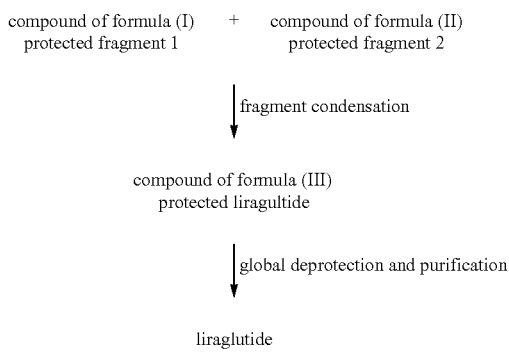

Scheme 1 compound of formula (I)    +    compound of formula (II)
protected fragment 1             protected fragment 2

↓ fragment condensation compound of formula (III)
protected liragultide

↓ global deprotection and purification liraglutide

Example 1-1: SPPS of Protected Fragment 1 with Pseudoproline

Protected fragment 1, that is protected Boc-His-(2-15)-Gly-OH, was synthesized by conventional Fmoc SPPS according to Scheme 2, wherein RESIN1 was a CTC resin, purchased from IRIS BioTech with loading capacity f=1.6 mmol/g, $Val^{(10)}$ and $Ser^{(11)}$ were coupled in form of a pseudo-Pro, Fmoc-Val-Ser(psi$^{Me,Me}$pro)-OH, the $His^{(1)}$ was coupled as Boc-$His^{(1)}$(Trt)-OH.

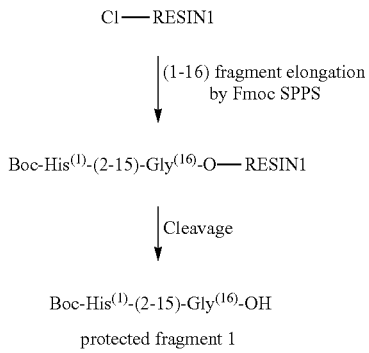

Scheme 2

Cl—RESIN1

↓ (1-16) fragment elongation by Fmoc SPPS

Boc-$His^{(1)}$-(2-15)-$Gly^{(16)}$-O—RESIN1

↓ Cleavage

Boc-$His^{(1)}$-(2-15)-$Gly^{(16)}$-OH protected fragment 1

The resin (2.01 g) was washed with DCM (3 times with 20 ml). Then the loading capacity of the resin was reduced to f=0.8 mmol/g by the addition of Fmoc-Gly-OH (0.5 eq; 0.478 g) and DIPEA (2 eq) in DCM (40 ml) and subsequent stirring for 2 h. Then the loading was checked by Fmoc determination and it was found to be f=0.71 mmol/g. Stepwise coupling of the other AAs was carried out at RT by adding the reagents AA:DIC:OxymaPure in the ratio 3 eq:3eq:3eq in 40 ml DMF and then stirring for 90 min. Removal of the Fmoc was done by treatment at RT with piperidine:DMF (2:8 v/v; 5 ml/g resin) for 1 time for 1 min and 1 time for 15 min. After each coupling, a ninhydrin test was done. In all cases except for $Phe^{(6)}$ and $His^{(1)}$, the ninhydrin test was negative. For $Phe^{(6)}$ and $His^{(1)}$, the coupling was repeated with stirring for 120 min instead of 90 min, and then the ninhydrin test was negative.

Cleavage of the Peptide—Resin Bond

After the introduction of the last amino acid, the resin was washed with DCM (5 ml/g; 5 time for 1 min), then washed with MeOH (5 ml/g; 5 time for 1 min) and dried. The protected fragment 1 was then cleaved from the resin using TFA/DCM (2/98 v/v; 40 ml; 3 times for 5 min). The TFA/DCM filtrates were collected and evaporated under vacuum. The residue was precipitated by addition of diisopropyl ether (40 ml), and isolated by filtration and drying under vacuum. Protected fragment 1 (2.93 g) was isolated with 81% yield and 92% purity. The purity was determined by HPLC.

Example 1-3: SPPS of Protected Fragment 2

Protected fragment 2, that is protected H-Gln-(18-31)-psWang, was synthesized by conventional Fmoc SPPS according to scheme 3, wherein RESIN2 was the CTC resin purchased from IRIS Biotech.

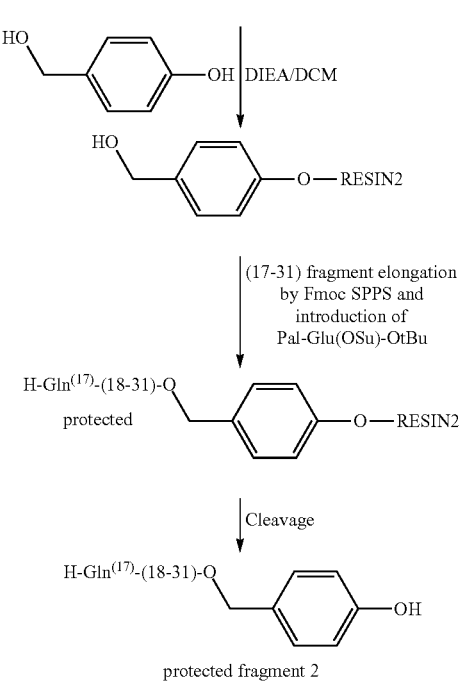

Scheme 3

Cl—RESIN2 protected fragment 2

4-Hydroxymethylphenol (0.3 eq) and DIPEA (2 eq) in DMF (60 ml) were added to the 2-CTC-resin (3 g, f=1.6 mmol/g), and after stirring for 2 h, MeOH (10 ml) was added to cap the unreacted Cl. Then Fmoc-Gly-OH (3 eq taking into account a loading of 0.5 mmol/g) was added together with DIC (3 eq) and DMAP (0.3 eq) in DMF (60 ml) and stirred for 90 min. Then the resin was treated for 10 min with Ac$_2$O: DIPEA 0.141 ml: 0.26 ml (1 eq) and the final loading as calculated by Fmoc determination was 0.45 mmol/g; the Fmoc determination also served for cleavage of Fmoc.

Coupling of the remaining AA was done by treatment at RT with AA:DIC:OxymaPure (3 eq: 3 eq: 3 eq) for 90 min. Removal of the Fmoc after each coupling was done by treatment at RT with piperidine:DMF (2:8 v/v, 5 ml/g resin) for 1 time for 1 min and 1 time for 15 min. After each coupling, the ninhydrin test was carried out. In all cases except Phe$^{(22)}$, Ala$^{18}$ and Gln$^{(17)}$ (Trt), the ninhydrin test was negative. For Phe$^{(22)}$, Ala$^{(18)}$, and Gln$^{(17)}$ (Trt), the coupling was repeated with stirring for 120 min instead of 90 min and then the ninhydrin test was negative.

Incorporation of Pal-Glu(OSu)-OtBu

After the coupling of Ala$^{(18)}$ and before the removal of its Fmoc protecting group, the Alloc protecting group of the side chain of Lys$^{(20)}$ was removed [by (i) washing the resin with DCM (5 times for 1 min each); (ii) treatment of the resin at RT with Pd(PPh$_3$)$_4$:PhSiH in the ratio 0.1eq:10eq (2 times for 10 min each in DCM); (iii) washing with DCM (5 times for 1 min each)], thereafter the resin was treated at RT with Pal-Glu(OSu)-OtBu (3 eq) and DIPEA (6 eq) in DCM (20 ml/g resin) for 16 hours. The ninhydrin test confirmed that the reaction was finished and the coupling of the last amino acid Fmoc-Gln(Trt)-OH was done followed by the N-terminal Fmoc deprotection. In order to completely remove the traces of piperidine, the peptide resin is extensively washed with DMF (5 times 50 ml DMF for 1 min each), DCM (5 times 50 ml DMF for 1 min each), 0.01% TFA in DCM (5 times 50 ml DMF for 1 min each).

Cleavage of Peptide-Resin Bond

The peptide-resin bond is cleaved by means of 2% v/v TFA in DCM (3 times 50 ml for 5 min). The filtrates are collected and evaporated under vacuum. The residue is precipitated in water (100 ml), filtered and dried under vacuum at 30±5° C. Yield was ca 50%, purity was ca 85%. The purity was determined by HPLC.

Example 1-4: Coupling of Protected Fragments 1 and 2 to Provide Protected Liraglutide Protected fragment 2 (900.0 mg, 1.0 eq, prepared according to example 1-3) was dissolved in DMSO (25 mL), the resulting solution was added to a solution of protected fragment 1 (795.5 mg, 1.1 eq), prepared according to example 1-1, in DMSO (25 mL), then PyBOP (1.1 eq) was added and the apparent pH is adjusted to 7.5 to 8.5 by dropwise addition of DIPEA. After 2.5 h the reaction was quenched by precipitation into 5 wt % aqueous NaHCO$_3$. The solid obtained after centrifugation was washed with 5 wt % aqueous citric acid. Yield: ca. 100% (ca. 1.6 g as it is).

Example 1-5: Global Deprotection of Protected Liraglutide

The protected liraglutide (1.8 g, prepared according to example 1-4) was added to ca. 18 ml of a mixture of TFA:phenol:water:TIS (88:5:5:2 v/v) of 0° C. The mixture was stirred 2 h at 0° C. and then poured into ether (200 ml) of 0° C. The precipitate was isolated by centrifugation and was washed with ether (3 times with 20 ml) and was dried under vacuum at 20±5° C. Yield ca. 100% (1.3 g as it is). Purity: 71%.

Example 1-6: Purification of Liraglutide

The following purification method is standard purification method which is not optimized for liraglutide and yield. Liraglutide, prepared according to example 1-5, was purified on XSelect® CSH C18 semi-preparative HPLC column (Waters). Mobile phase A: 0.1% (v/v) TFA in water. Mobile phase B: 0.1% TFA (v/v) in acetonitrile Gradient:

| t [min] | A [%] | B [%] |
| --- | --- | --- |
| 0 | 95 | 5 |
| 3 | 95 | 5 |
| 4 | 51 | 49 |
| 9 | 48.5 | 51.5 |
| 10 | 0 | 100 |
| 12 | 0 | 100 |
| 12.5 | 95 | 5 |

Liraglutide elutes at about minute 7 of the gradient. Purity: >99%. Purification yield: 10%.

---

The invention claimed is:

1. A method for the preparation of a peptide (PEP) which comprises a coupling in liquid phase of two peptide fragments, an N-terminal fragment (FRAG1) of peptide (PEP) and a C-terminal fragment (FRAG2) of peptide (PEP);

wherein the C-terminal COOH of the C-terminal fragment (FRAG2) is protected by a psWang residue; the psWang residue is a residue of formula (psWang);

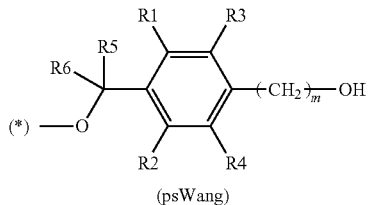

(psWang)

wherein (*) denotes the covalent bond to the C atom of the CO residue of the C-terminal COOH of the C-terminal fragment (FRAG2);

R1, R2, R3 and R4 are identical or different and independently from each other selected from the group consisting of H, $C_{1-4}$ alkyl, $C_{1-4}$ alkoxy, CN, F, Cl and Br;

R5 and R6 are identical or different and are, independent from each other, H or $C_{1-4}$ alkyl;

m is 0, 1, 2, 3, 4, 5, 6, 7, 8, 9 or 10;

wherein the C-terminal fragment (FRAG2) is prepared by a solid phase peptide synthesis (SPPS);

wherein the psWang linker or the psWang residue respectively is connected to a first resin used for the solid phase peptide synthesis (SPPS) by an ether bond (ETHBOND2);

wherein the ether bond (ETHBOND2) is cleavable under weakly acidic conditions using trifluoroacetic acid (TFA), trifluoroethanol (TFE), or hexafluoroisopropanol (HFIP); and wherein the first resin is selected from the group consisting of a chlorotritykhloride

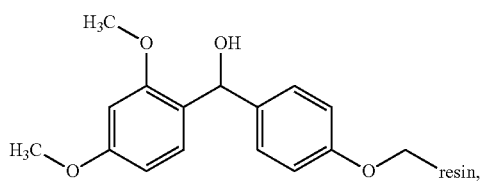

(CTC) resin, a Rink acid resin a SASRIN resin

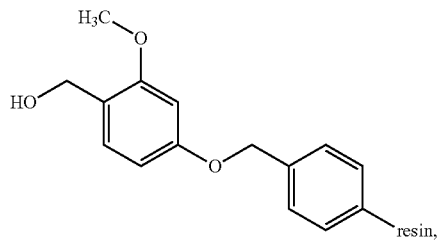

a resin modified with 5-(4-hydroxymethyl-3,5-dimethoxyphenoxy)valeric acid (HAL), and a resin modified with 4-(4-hydroxymethyl-3-methoxyphenoxy)butyric acid (HMPB); wherein the Rink acid resin, the SASRIN resin, the resin modified with HAL, and the resin modified with HMPB are used in the chlorinated form.

2. The method according to claim 1, wherein R1, R2, R3 and R4 are identical or different and independently from each other selected from the group consisting of H, $C_{1-2}$ alkyl, $C_{1-2}$ alkoxy and Cl; and R5 and R6 are identical or different and are independently from each other H or $C_{1-2}$ alkyl.

3. The method according to claim 1, wherein m is 0, 1, 2, 3 or 4.

4. The method according to claim 1, wherein m is 0 and R1, R2, R3, R4, R5 and R6 are H.

5. The method according to claim 1, wherein the N-terminal $NH_2$ of the N-terminal fragment (FRAG1) is protected by a protecting group (PROTGN) during the coupling of the N-terminal fragment (FRAG1) and the C-terminal fragment (FRAG2).

6. The method according to claim 1, wherein any amino acid residue of the N-terminal fragment (FRAG1) and the C-terminal fragment (FRAG2), that can be used in a side chain protected form, is used in a side chain protected form.

7. The method according to claim 1, wherein the N-terminal fragment (FRAG1) is prepared by solid phase peptide synthesis (SPPS) using a second resin.

8. The method according to claim 7, wherein the C-terminal amino acid of the N-terminal fragment (FRAG1) is connected to the second resin used for the solid phase peptide synthesis (SPPS) with an ester bond (ESTBOND1).

9. The method according to claim 8, wherein the ester bond (ESTBOND1) is cleaved under weakly acidic conditions using trifluoroacetic acid (TFA), trifluoroethanol (TFE), or hexafluoroisopropanol (HFIP).

10. The method according to claim 8, further comprising cleaving the ester bond (ESTBOND1) under weakly acidic conditions using trifluoroacetic acid (TFA), trifluoroethanol (TFE), or hexafluoroisopropanol (HFIP).

11. The method according to claim 10, wherein the ester bond (ESTBOND1) is cleaved under weakly acidic conditions using a mixture of from 0.01 to 25% trifluoroacetic acid (TFA) in a solvent which is inert against the trifluoroacetic acid (TFA).

12. The method according to claim 1, wherein the first resin is a chlorotritylchloride (CTC resin).

13. The method according to claim 1, wherein the N-terminal fragment (FRAG1) and the C-terminal fragment (FRAG2) are prepared by solid phase peptide synthesis (SPPS) using Fmoc/tBu strategy.

14. The method according to claim 1, wherein peptide (PEP) is liraglutide, and the (*) in formula (psWang) denotes the covalent bond to the C atom of the CO residue of $Gly^{(31)}$ of liraglutide.

15. The method according to claim 1, wherein the N-terminal fragment (FRAG1) is) Boc-$H^{(1)}$ $AEGT^{(5)}$ $FTSDV^{(10)}$ $SSYLE^{(15)}$ $G^{(16)}$-OH (SEQ ID NO: 1); and the C-terminal fragment (FRAG2) is H-$Q^{(17)}$ $AAK^{(20)}$ (Palmitoyl-Glu-OtBu)$EFIAW^{(25)}$ $LVRGR^{(30)}$ $G^{(31)}$-psWang (SEQ ID NO: 2).

16. The method according to claim 15, wherein the Palmitoyl-Glu-OtBu residue on the $N^6$ of the $Lys^{(20)}$ of the C-terminal fragment (FRAG2) is a residue of formula (PALGLU),

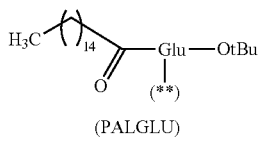

(PALGLU)

with the (**) in formula (PALGLU) denoting the covalent bond between the COOH of the side chain of the Glu and the $N^6$ of the $Lys^{(20)}$, and the Palmitoyl-Glu-OtBu residue is covalently bonded to the $Lys^{(20)}$ in a reaction (REACPALGLU), wherein the $NH_2$ of the side chain of the Lys is reacted with a precursor of the residue of formula (PALGLU);

reaction (REACPALGLU) is done before the C-terminal fragment (FRAG2) is cleaved from the first resin.

17. The method according to claim 16, wherein the precursor of the residue of formula (PALGLU) is a compound of formula (10);

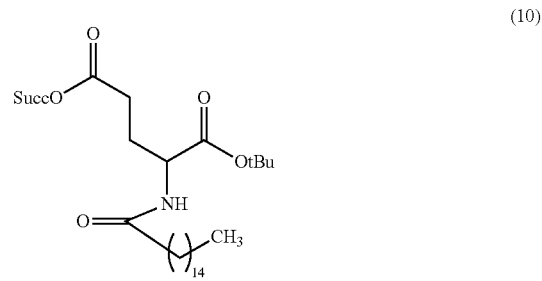

with SuccO being a residue of formula (SuccO);

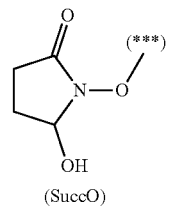

wherein the (***) denotes the covalent bond to the CO residue in the compound of formula (10).

18. The method according to claim 16, wherein the reaction (REACPALGLU) is done after the coupling of $Ala^{(19)}$ or after the coupling of $Ala^{(18)}$, and before removal of the protecting group of the alpha $NH_2$ of $Ala^{(19)}$ or of $Ala^{(18)}$ respectively.

19. The method according to claim 1, further comprising cleaving the ether bond (ETHBOND2) under weakly acidic conditions using trifluoroacetic acid (TFA), trifluoroethanol (TFE), or hexafluoroisopropanol (HFIP).

20. The method according to claim 19, wherein the ether bond (ETHBOND2) is cleaved under weakly acidic conditions using a mixture of from 0.01 to 25% trifluoroacetic acid (TFA) in a solvent which is inert against the trifluoroacetic acid (TFA).

21. The method according to claim 19, wherein the method comprises two steps, a step STEP1 and a step STEP2; wherein step STEP1 comprises the coupling of the N-terminal fragment (FRAG1) and the C-terminal fragment (FRAG2) by liquid phase peptide synthesis;
wherein step STEP1 provides a peptide (PEP-psWang);
wherein step STEP2 comprises cleavage of psWang from the peptide (PEP-psWang) obtained in step STEP1.

* * * * *